United States Patent
Stillman et al.

(10) Patent No.: US 7,225,681 B2
(45) Date of Patent: Jun. 5, 2007

(54) STATISTICAL METHOD FOR IDENTIFYING MICROCRACKS IN INSULATORS

(75) Inventors: Daniel J. Stillman, Dallas, TX (US); Nancy R. Ota, Keller, TX (US); Cheryl Hartfield, McKinney, TX (US)

(73) Assignee: Texas Instruments Incorporated, Dallas, TX (US)

( * ) Notice: Subject to any disclaimer, the term of this patent is extended or adjusted under 35 U.S.C. 154(b) by 183 days.

(21) Appl. No.: 11/145,673

(22) Filed: Jun. 6, 2005

(65) Prior Publication Data

US 2006/0273780 A1    Dec. 7, 2006

(51) Int. Cl.
*G01N 19/08*    (2006.01)

(52) U.S. Cl. .............................. 73/799; 73/762; 73/826; 73/852

(58) Field of Classification Search .................. 73/762, 73/799, 826, 851
See application file for complete search history.

(56) References Cited

U.S. PATENT DOCUMENTS

| | | | | |
|---|---|---|---|---|
| 3,710,616 A | * | 1/1973 | Smith et al. | 205/791.5 |
| 3,803,485 A | * | 4/1974 | Crites et al. | 324/693 |
| 4,400,618 A | * | 8/1983 | Bupp et al. | 250/302 |
| 4,484,132 A | * | 11/1984 | Crites | 324/557 |
| 4,531,400 A | * | 7/1985 | Nevel | 73/12.13 |
| 4,774,188 A | * | 9/1988 | Chandross | 436/5 |
| 4,864,867 A | * | 9/1989 | Manahan, Sr. | 73/851 |
| 5,005,423 A | * | 4/1991 | Poormon | 73/799 |
| 5,165,287 A | * | 11/1992 | Manahan, Sr. | 73/851 |
| 6,840,083 B2 | * | 1/2005 | Hijikata | 73/12.01 |
| 7,080,561 B2 | * | 7/2006 | Bohlmann et al. | 73/800 |

\* cited by examiner

*Primary Examiner*—Edward Lefkowitz
*Assistant Examiner*—Freddie Kirkland, III
(74) *Attorney, Agent, or Firm*—Yingsheng Tung; Wade James Brady, III; Frederick J. Telecky, Jr.

(57) ABSTRACT

One embodiment of the invention is a method for evaluating a material such as low-k dielectric, by a stress-generating test tool such as a needle. The evaluation object is shaped as a stack of adhering layers: low-k dielectric, first metal (preferably copper), barrier metal (preferably tantalum nitride), and second metal (preferably aluminum). A numerical correlation is established between a cracking in the barrier metal layer caused by probing and a damage in the layer of insulating material-to-be-tested.

A predetermined number of locations of the top metal layer is selected for the probing step comprising touch-down, applying force, and lifting is repeated so that the number of repeats provide a pre-determined statistical confidence level.

The top metal layer is then removed by a chemical etch solution so that the etch solution also penetrates into any stress-created cracks of the barrier metal layer underneath the imprints, and further dissolves a portion of the first metal layer, generating cavities in the first metal layer. The occurrence of all first metal cavities is recorded and correlated with the probing.

7 Claims, 4 Drawing Sheets

STATISTICAL METHOD FOR IDENTIFYING MICROCRACKS IN INSULATORS

FIELD OF THE INVENTION

The present invention is related in general to the field of semiconductor device fabrication and more specifically to a method for evaluating mechanically weak dielectrics relative to their sensitivity of cracking under mechanical stress, and for evaluating multiprobe test cards relative to their tendency to generate cracks in mechanically weak dielectrics.

DESCRIPTION OF THE RELATED ART

The functionality of semiconductor integrated circuits (IC) is typically tested twice: The first test is performed while the semiconductor chips incorporating the circuits are still in wafer form. This test is a direct-current (dc) test not requiring any cooling of the circuit and evaluates a set of circuit parameters ("parametric test"). The second test is performed after encapsulating and packaging each singulated chip. This test is an alternating-current (ac) test and evaluates primarily the speed of the circuit ("functional test").

The parametric test is typically performed by a cantilever probe card, which contains one individual tungsten-rhenium needle, shaped as a cantilever with a bend and a tapered tip, for each circuit contact pad. Because of the high number of contact pads of contemporary circuits (for some circuits more than 1000 pads), the probe card contains a high number of probe needles in dense arrangement; it is a "multiprobe" card and the parametric test is often referred to as the multiprobe test.

During the multiprobe test, the needles are pressed against the metal of the contact pads, commonly aluminum, with a pressure high enough to break through the aluminum oxide film and establish ohmic contact with the pad metal for a reliable electrical reading. It is well known that cantilever probe cards may inflict damage to the metal pads of the device-under-test (DUT) in the form of cracks in the barrier metal and/or the dielectric material under the pads. The damage can oft be mitigated by controlling the balanced contact force (BCF) of the probe card needles. By making alterations in the needle geometry, the BCF can be modified higher or lower. The probe card is typically designed to customer supplied specifications for BCF, and the vendors use their best practices to create a needle geometry that meets the customer's target BCF. The customer's acceptance of a new card design relies on analytical confirmation of BCF values through measurements of contact force on a probe card analyzer.

Recent technological developments in the semiconductor industry tend to aggravate the probe card induced damages. For instance, newer low-k dielectric materials such as silicon-containing hydrogen silsesquioxane (HSQ) are being introduced due to their lower dielectric constant, which helps to reduce the capacitance C in the RC time constant and thus allows higher circuit speed. Since the density and porosity of dielectric films affect the dielectric constant through absorption or desorption of water, films with these characteristics are introduced even when they are mechanically weaker. Films made of aerogels, organic polyimides, and parylenes fall into the same category. These materials are less dense and mechanically weaker than previous standard insulators such as the plasma-enhanced chemical vapor deposited dielectrics. This trend even affects stacks of dielectric layers such as alternating layers of plasma-generated tetraethylorthosilicate (TEOS) oxide and HSQ, or ozone TEOS oxide and HSQ. Since these material are also used under the bond pad metal, they magnify the risk of device failure by cracking.

SUMMARY OF THE INVENTION

Applicants recognize a need for a straightforward solution based on methods practiced by production. A careful investigation showed that two probe cards, each from a different vendor and built to the same specification, including the same BCF value, had dramatically different results in the amount of damage by metal barrier and dielectric cracks inflicted on low-k dielectric devices. A new method to assess "goodness" of a probe card design on new semiconductor technology is required.

The investigation showed that the solution is the implementation of a statistical method, which provides a systemic way to empirically measure the propensity of a probe card to inflict unacceptable damage to the DUT. The method requires two starting items: A wafer, which is representative of production material; and a probe card, which is to be qualified for use in production. A wafer map is created to delineate sections of the wafer that will be probed with various parameters. Typical parameters of interest include probe overtravel, number of touchdowns, needle, or card, design, and BCF. One, several, or all of these parameters may be evaluated. The number of chips to be probed for assessment of each parameter is determined based on desired statistical significance.

After probing according to the wafer map and completing the probe parameter matrix, a thorough evaluation of probe-inflicted damage is carried out in the following steps:

1. Inspection of as-received scrub marks, including photo documentation. A single representative photo for needles from each card tier is required, along with photos of any scrub marks that stand out as being abnormal.
2. To easily visualize cracks, the wafer may be sawed into segments. Photos after sawing are acquired as described above.
3. To highlight cracks, de-layering of the device is performed one layer at a time, followed by inspection (and photo documentation), until all layers of concern have been inspected. The number of pads inspected for damage in each probe parameter section must represent statistically valid sampling.
4. When a probe card is to be evaluated, the observed probe damage is compared against the production parameter requirements to assess, whether the probe card design and the vendor are acceptable.

One embodiment of the invention uses a card with relatively few needles to test the robustness of the low-k material; another embodiment of the invention uses a card with the full high number of needles to test the card capability.

One embodiment of the invention is a method for evaluating a material by a stress-generating test tool. The first step of the method provides an elongated elastic probing tool shaped to transmit force to a probing tip. The next step provides an evaluation object shaped as a stack of adhering layers, including sequentially a layer of an insulating material-to-be-tested (preferably low-k dielectric), a layer of a first metal (preferably copper), a layer of a barrier metal (preferably tantalum nitride), and a top layer of a second metal (preferably aluminum) The second metal is ductile relative to the first metal.

A numerical correlation is established between a cracking in the barrier metal layer caused by probing and a damage in the layer of insulating material-to-be-tested.

In the next process step, a first location of the top metal layer is selected. This first location is probed by touching the tool down on the first location, and exerting a controlled amount of force so that the tip generates an imprint while concurrently generating compressive and shear stress in the sequential layers under the top metal layer. The tool is then lifted from the first location and the probing step is repeated a predetermined number of times at the selected first location.

A predetermined number of fresh locations of the top metal layer is selected, and the probing step is repeated so that the number of repeats provide a pre-determined statistical confidence level.

In the next process step, the top metal layer is removed by a chemical etch solution so that the etch solution also penetrates into any stress-created cracks of the barrier metal layer underneath the imprints, and further dissolves a portion of the first metal layer, generating cavities in the first metal layer. The occurrence of all first metal cavities is recorded and correlated with the probing.

The technical advantages represented by certain embodiments of the invention will become apparent from the following description of the preferred embodiments of the invention, when considered in conjunction with the accompanying drawings and the novel features set forth in the appended claims.

DETAILED DESCRIPTION OF THE PREFERRED EMBODIMENTS

Figure 1:
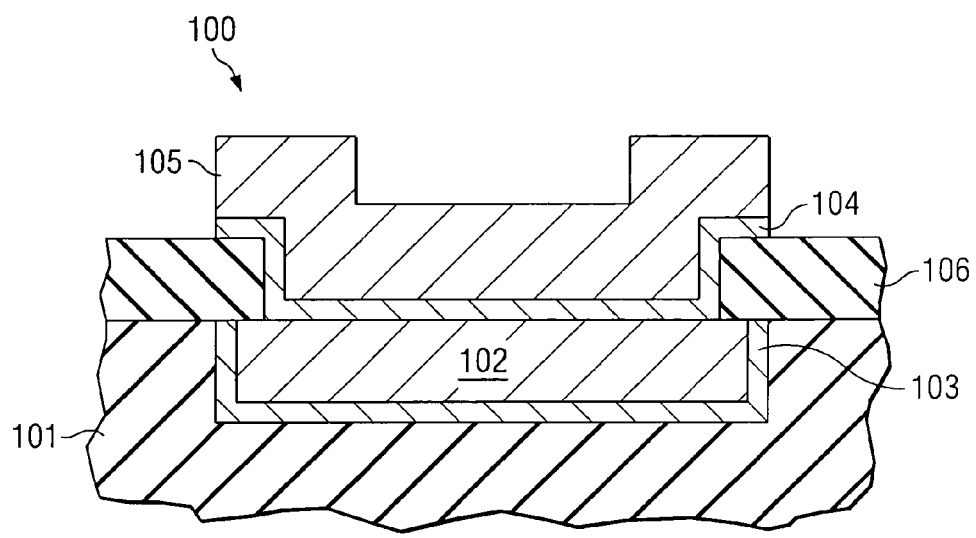
FIG. 1 is a schematic cross section of an embodiment of the invention illustrating the evaluation object, including the insulating material-to-be-tested.

The schematic cross section of FIG. 1 illustrates an evaluation object of the invention, generally designated 100. The evaluation object is shaped as a stack of adhering layers, which include sequentially a layer 101 of the insulating material-to-be-tested; of special interest is an evaluation of its mechanical robustness. Of specific interest as layer 101 are low-k dielectric materials used in the semiconductor technology for reducing the capacitance in the RC time constant and thus for producing high-speed integrated circuits (ICs). Examples of low-k materials include silicon-containing hydrogen silsesquioxane (HSQ), aerogels, organic polyimides, and parylenes, stacks of dielectric layers such as alternating layers of plasma-generated tetraethylorthosilicate (TEOS) oxide and HSQ, or ozone TEOS oxide and HSQ.

Embedded in the low-k dielectric material 101 is a first metal 102, preferably copper of about 400 to 600 nm thickness, which may be surrounded by a barrier metal layer 103, preferably made of tantalum nitride in the thickness range from about 5 to 7 nm. The conductor 102 is topped by a barrier metal layer 104, preferably tantalum nitride of about 50 to 70 nm thickness. The outermost layer 105 of the evaluation object 100 is a second metal, preferably formed by aluminum in the thickness range from about 0.5 to 1.2 μm. Other top layer may include copper-doped aluminum. Second metal 105 is ductile relative to first metal 102. 106 denotes an overcoat, which protects the IC as a moisture-impermeable layer; it is preferably made of silicon nitride or silicon oxynitride.

Figure 2:
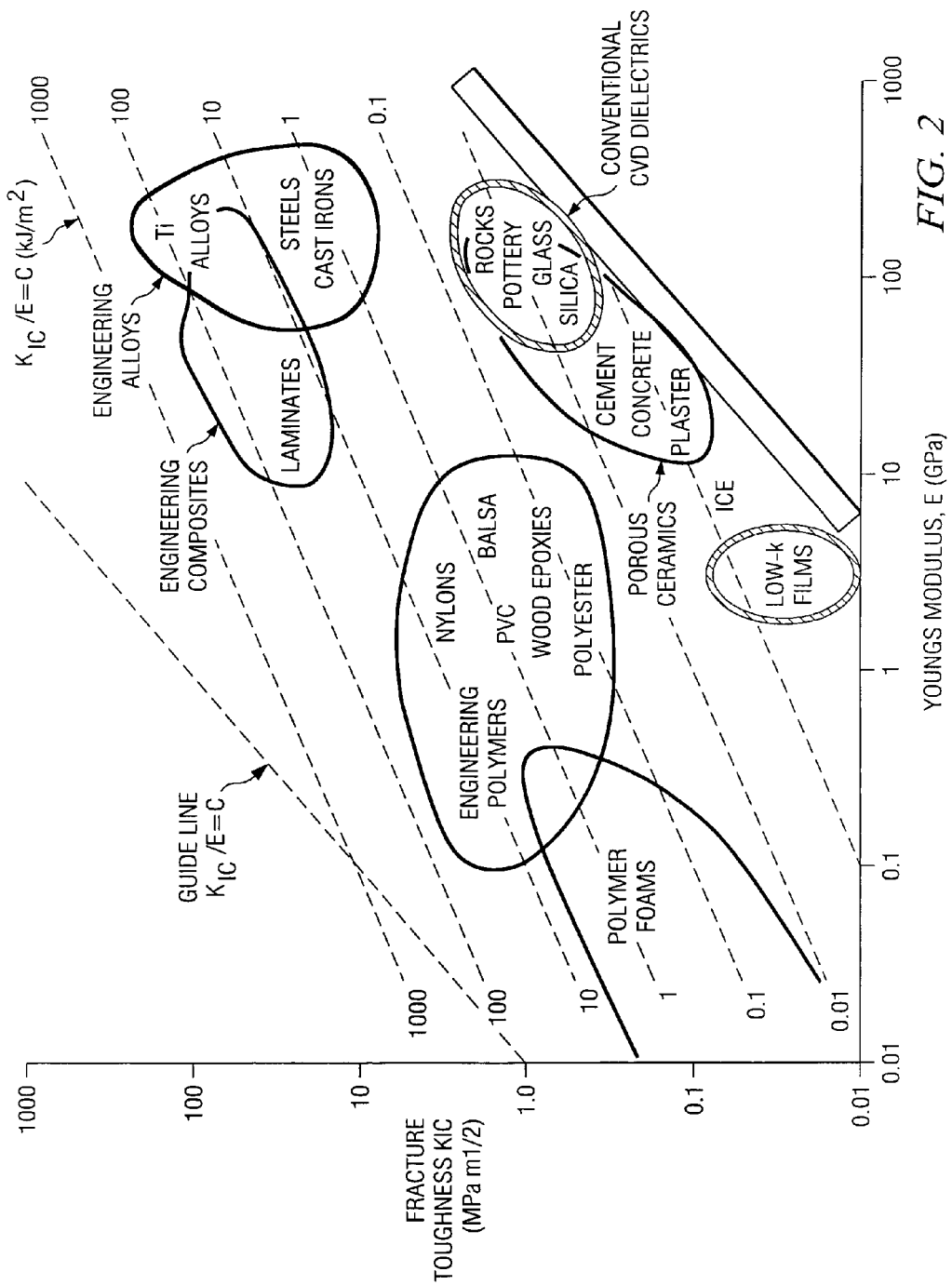
FIG. 2 plots fracture toughness as a function of Young's modulus to illustrate the challenge bought about by the low-k materials.

FIG. 2 compares properties of the low-k dielectric materials with related materials. The fracture toughness (measured in MPa·m½) is plotted as a function of YOUNGs modulus (measured in GPa). FIG. 1 clearly illustrates that the low-k dielectrics are mechanically weak and offer only little fracture toughness. They are in a class of their own compared to the conventional chemical vapor deposited (CVD) dielectrics, which offer much higher fracture toughness. Consequently, the reliability of low-k materials represents a challenge for the semiconductor device engineer, especially since the conventional technology offers no industry method for measuring low-k layer fracture toughness.

Figure 3:
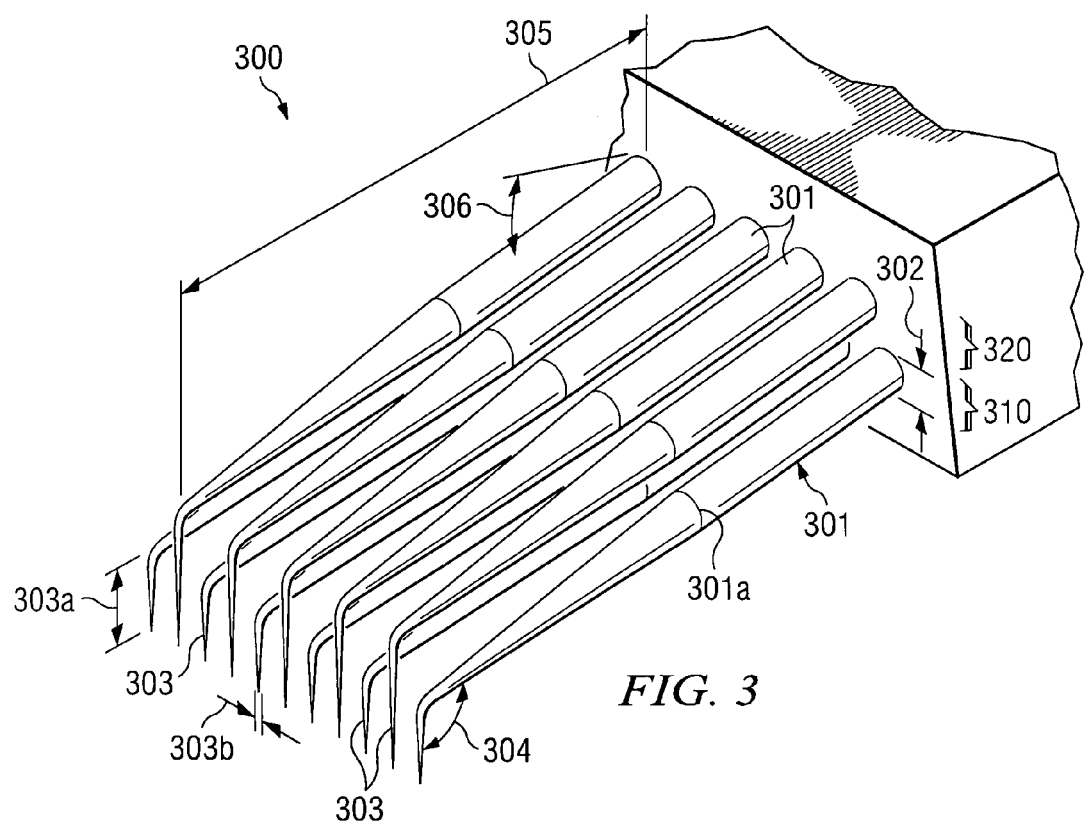
FIG. 3 is a perspective view of a preferred probing tool used to evaluate the material-to-be-tested.

The perspective view of FIG. 3 illustrates a preferred evaluation tool generally designated 300. The tool consists of at least one elongated elastic probing needle 301, preferably made of tungsten-rhenium (another option is copper-beryllium) with a certain diameter 302 (for instance, 75 to 125 μm), tapering from a certain point 301a and finally bending to a probing tip 303, which has a length 303a and a diameter 303b. An example for the tip diameter 303b is 10 μm and thus at least one order of magnitude smaller than the locations (for instance, the IC contact pads) of the top metal 105 to be tested. The bending angle is designated 304. The length 305 of the needle has a certain angle 306 and thus forms a cantilever. The evaluation tool 300 is designed to elastically transmit force to the probing tip and thus to the evaluation object.

Figure 4:
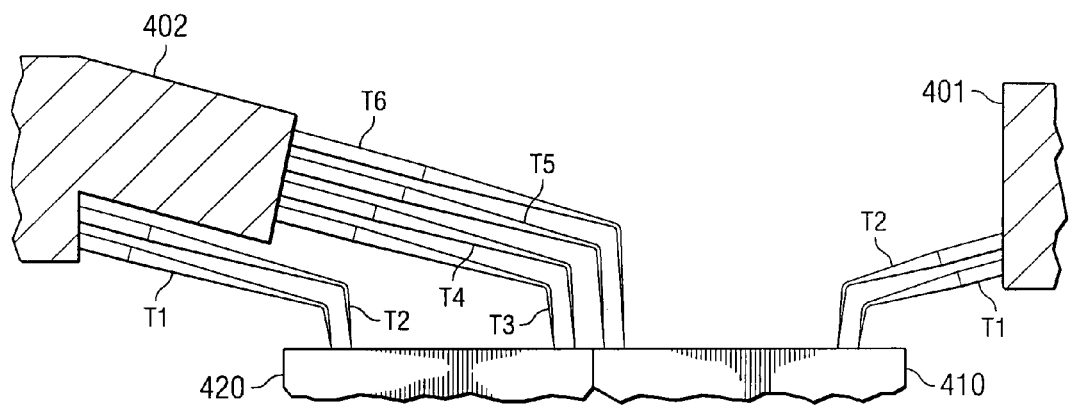
FIG. 4 is a schematic cross section of a plurality of evaluation tools arranged for multiple simultaneous probings.

FIG. 3 actually shows two tiers 310 and 320 of needles arranged to take multiple tests and readings at one time. Large sample sizes are required for achieving good statistics; the higher the confidence level, the greater the sampling volume, which is required. The statistical significance of the data can be set to any level by varying the confidence limit and/or the desired defective part per million level (dppm). The schematic cross section of FIG. 4 illustrates a plurality of needle tiers, held by two shelves 401 and 402 and simultaneously probing two semiconductor IC chips 410 and 420. With probing tool arrangements as depicted in FIG. 4, evaluation of sample sizes on the order of thousands are feasible. This level of probing permits the detection of defect rates of 1000 defective parts per million (dppm) or less with 90% confidence. The method can thus be applied for process control, rather than used only as a failure analysis tool, where very few samples are typically examined.

Figure 5:
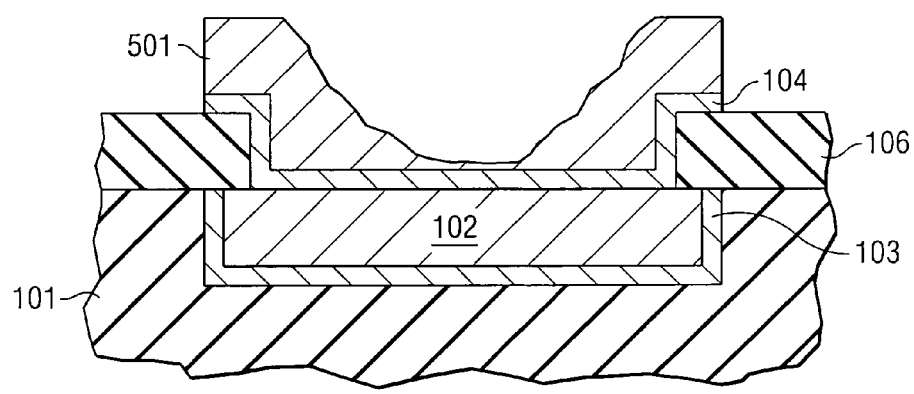
FIG. 5 is a schematic cross section of the evaluation object of FIG. 1 of the invention after the probing by the evaluation tool has been performed.

The schematic cross section of FIG. 5 illustrates the effect of probing by the elastic needles on the evaluation object of FIG. 1. The originally flat layer 105 of the second metal is deformed to layer 501, showing an imprint and smearing of the ductile second metal (preferably aluminum). The probing is performed with the following sequence of process steps:

Selecting a first location of top metal layer 105;

probing the first location by touching the probing tool (an elastic needle 301) down on the first location, and exerting a controlled amount of force by the tool so that the tip 303 generates an imprint while concurrently generating compressive and shear stress in said sequential layers 104, 102, 103, and 101 under the top metal layer;

lifting the tool from the first location and repeating the probing step a predetermined number of times at the selected first location;

selecting a predetermined number of fresh locations of the top metal layer and repeating the probing step so that the number of touchings provide a pre-determined statistical confidence level.

With each new cycle of selecting a fresh location and the consecutive steps of probing and lifting, one more repetition may be added.

Figure 6:
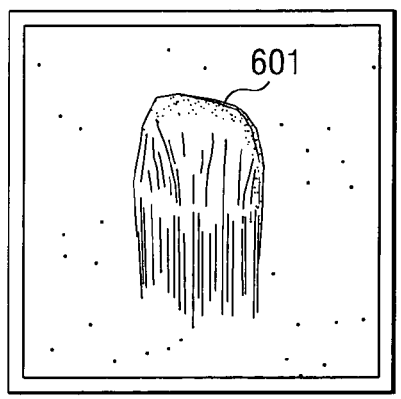
FIG. 6 represents schematically a first kind of imprint in the evaluation object by a probing tool.
Figure 7:
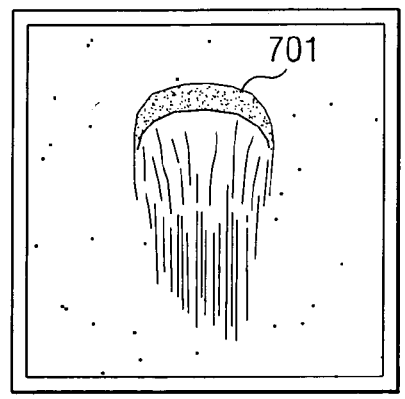
FIG. 7 represents schematically a second kind of imprint in the evaluation object by a probing tool.

Detailed analysis of the imprints has revealed two classes of imprints as depicted in FIGS. 6 and 7. The first class 601, shown in FIG. 6, turned out to cause far more damage such as cracking of the barrier layer 104 (see de-processing steps below) than the second class 701, shown in FIG. 7. Further detailed analysis has established a numerical correlation between a cracking in the barrier layer 104 caused by the probing and a damage in the layer 101 of the insulating material-to-be-tested. That numerical correlation is approximately 90%.

Figure 8:
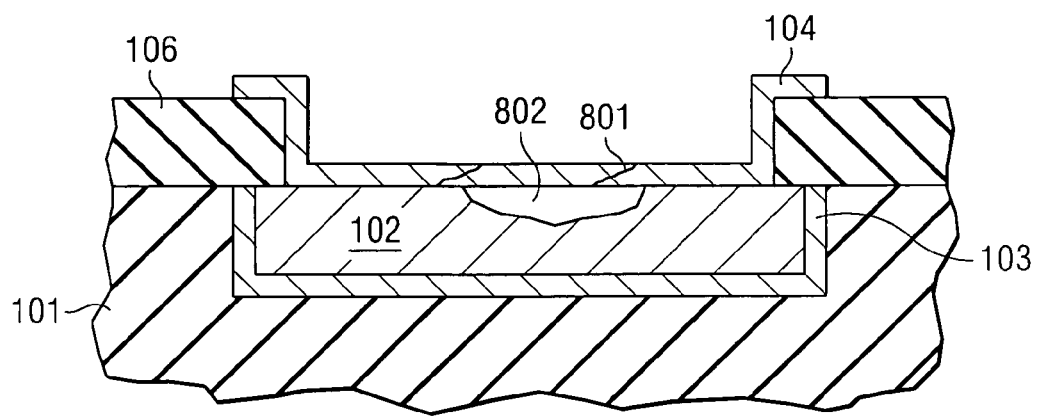
FIG. 8 is a schematic cross section of the evaluation object of FIG. 5 after the removal of the top metal layer.

In order to provide the evidence of a crack in barrier layer 104, and thus by implication in the insulator-to-be-tested, which can be detected under a microscope, the following sequence of de-processing steps are applied:

FIG. 8: Removing the top metal layer by a chemical etch solution so that the etch solution also penetrates into any stress-created cracks 801 of the barrier metal layer 104 underneath the imprints (see FIGS. 6 and 7), and further dissolves a portion 802 of the first metal layer 102, generating cavities 802 in the first metal layer. This step is performed to highlight the cracks. The procedure will vary depending on the material beneath the probed pad. In embodiments of metal pad overlaying a barrier covering a second metal, as shown in FIGS. 1 and 8, a wet etch is advantageous to seep through the crack and etch metal underlying the pad, increasing the size of the damage area and enabling easy visualization and detection. In other embodiments of pad metal overlying a barrier covering a dielectric, it may be necessary to remove both the pad metal and the barrier, to view any metal attacked beneath a cracked dielectric;

recording the occurrence of all first metal cavities 802; and correlating the occurrence of the cavities with said probing and the probe marks 601 and 701. It is also desirable to note any repeating patterns indicative of a damaged needle, and to distinguish tiers for better understanding of card design implications.

The process steps for calculating the sample size needed for detecting a given dppm level are as follows:

Assuming that the proportion of cracked pads has a binomial distribution.

Relying on the Chi squared approximation to a binomial distribution, calculating the total sample number required for an estimated dppm of zero when 90% upper confidence level is at most X dppm. X is determined by the user. X is the maximum dppm level the user desires to have capability to detect.

Calculating the total sample count, which is the sample size required to detect the desired defect level. Evaluation of a smaller sample size will prevent detection of defects at the desired defect density detection limits.

As an example, for an upper dppm confidence limit of 1000 dppm using 90% confidence interval when zero cracked pads are observed, the sample size requirement for evaluation must be at least 2,302 pads.

The process step for calculating the dppm level for a given sample size is as follows:

If the defect detectivity targets are not set beforehand, using the same methods to determine the upper dppm limit at 90% confidence interval, given a set number of cracked pads from a given number evaluated.

As an example, at 90% confidence interval, zero cracked pads of 500 examined pads corresponds to an upper limit of 4605 dppm.

In another embodiment of the invention, the method is not used with the relatively few needles required for testing the robustness of dielectric materials, but rather with a complete multiprobe card containing often 1000 or more needles. This embodiment provides the testing of the card capability and the quality of the vendor. A wafer map is created to delineate sections of the wafer that will be probed with various parameters. Typical parameters of interest include probe overtravel, number of touchdowns, needle and card design, and balanced contact force. The number of chips to be probed for assessment of each parameter is determined based on desired statistical significance. For example, 2500 bond pads may be evaluated for detectability at a dppm level of X amount at 95% confidence interval. The wafer level may ideally include a region that will not be probed; it is beneficial in cases where the wafer may have been already probed, prior to receipt for use in the method.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

We claim:

1. A method for evaluating a material by a stress-generating test tool, comprising the steps of:

providing an elongated elastic probing tool shaped to transmit force to a probing tip;

providing an evaluation object shaped as a stack of adhering layers, including sequentially a layer of an insulating material-to-be-tested, a layer of a first metal, a layer of a barrier metal, and a top layer of a second metal, said second metal ductile relative to said first metal;

establishing a numerical correlation between a cracking in the barrier metal layer caused by probing and a damage in the layer of insulating material-to-be-tested;

selecting a first location of said top metal layer;

probing said first location by touching said tool down on said first location, and exerting a controlled amount of force by said tool so that said tip generates an imprint while concurrently generating compressive and shear stress in said sequential layers under said top metal layer;

lifting said tool from said first location and repeating said probing step a predetermined number of times at said selected first location;

selecting a predetermined number of fresh locations of said top metal layer and repeating said probing step so that the number of touchings provide a pre-determined statistical confidence level;

removing said top metal layer by a chemical etch solution so that said etch solution also penetrates into any stress-created cracks of said barrier metal layer underneath said imprints, and further dissolves a portion of said first metal layer, generating cavities in said first metal layer;

recording the occurrence of all first metal cavities; and correlating said occurrence of said cavities with said probing.

2. The method according to claim 1 further comprising the step of adding one repetition with each new cycle of selecting a fresh location and consecutive steps of probing and lifting.

3. The method according to claim 1 wherein said elongated elastic tool is a tungsten-rhenium needle having a bent, tapered end, which terminates in a tip having a diameter at least one order of magnitude smaller than said top metal locations tested.

4. The method according to claim 1 wherein said insulating material-to-be-tested is a low-k dielectric insulator.

5. The method according to claim 1 wherein said first metal is copper.

6. The method according to claim 1 wherein said barrier metal is tantalum nitride.

7. The method according to claim 1 wherein said second metal includes aluminum.

* * * * *